United States Patent
Wang et al.

(10) Patent No.: US 11,123,710 B2
(45) Date of Patent: Sep. 21, 2021

(54) HYDROGENATION CATALYST

(71) Applicant: HONEYWELL INTERNATIONAL INC., Morristown, NJ (US)

(72) Inventors: Haiyou Wang, Amherst, NY (US); Hsueh S. Tung, Getzville, NY (US); Daniel C. Merkel, Orchard Park, NY (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

(21) Appl. No.: 13/857,013

(22) Filed: Apr. 4, 2013

(65) Prior Publication Data

US 2013/0225882 A1 Aug. 29, 2013

Related U.S. Application Data

(63) Continuation of application No. 12/534,323, filed on Aug. 3, 2009, now abandoned.

(51) Int. Cl.
| | |
|---|---|
| *B01J 32/00* | (2006.01) |
| *B01J 23/44* | (2006.01) |
| *C07C 17/354* | (2006.01) |
| *B01J 23/48* | (2006.01) |
| *B01J 23/40* | (2006.01) |
| *B01J 35/10* | (2006.01) |
| *B01J 21/04* | (2006.01) |

(Continued)

(52) U.S. Cl.
CPC ........... *B01J 23/44* (2013.01); *B01J 21/04* (2013.01); *B01J 23/36* (2013.01); *B01J 23/40* (2013.01); *B01J 23/48* (2013.01); *B01J 23/70* (2013.01); *B01J 35/1014* (2013.01); *B01J 37/18* (2013.01); *C07C 17/354* (2013.01)

(58) Field of Classification Search
None
See application file for complete search history.

(56) References Cited

U.S. PATENT DOCUMENTS

| | | | |
|---|---|---|---|
| 2,657,980 | A | 11/1953 | Sprauer |
| 2,875,158 | A | 2/1959 | Winstrom |

(Continued)

FOREIGN PATENT DOCUMENTS

| | | |
|---|---|---|
| CN | 1235561 A | 11/1991 |
| CN | 1086802 A | 5/1994 |

(Continued)

OTHER PUBLICATIONS http://www.cdc.gov/niosh/npg/npgd0021.html—downloaded Jan. 11, 2015.*

(Continued)

*Primary Examiner* — Clinton A Brooks
(74) *Attorney, Agent, or Firm* — Colleen D. Szuch

(57) ABSTRACT

The present invention relates, in part, to an alpha-alumina support for a hydrogenation catalyst useful in hydrogenating fluoroolefins. In certain aspects, it relates to a method for hydrogenating a compound by contacting an olefin reactant having at least one carbon-fluorine bond, with a supported hydrogenation catalyst. The reaction results in a product that includes a hydrogenated derivative of the olefin. In certain embodiments, the supported hydrogenation catalyst includes a zero-valent metal disposed on an alpha-alumina support.

10 Claims, 1 Drawing Sheet

(51) Int. Cl.
*B01J 37/18* (2006.01)
*B01J 23/70* (2006.01)
*B01J 23/36* (2006.01)

(56) References Cited

U.S. PATENT DOCUMENTS

| | | | |
|---|---|---|---|
| 2,908,654 A | 10/1959 | Heinemann et al. | |
| 3,862,252 A * | 1/1975 | Matsumura et al. | 585/273 |
| 3,904,701 A | 9/1975 | Schultz et al. | |
| 4,158,737 A | 6/1979 | Bartsch | |
| 4,404,124 A | 9/1983 | Johnson et al. | |
| 4,762,956 A | 8/1988 | Liu et al. | |
| 4,800,075 A | 1/1989 | Jenkins | |
| 4,940,687 A | 7/1990 | Liu et al. | |
| 5,396,000 A | 3/1995 | Nappa et al. | |
| 5,587,348 A | 12/1996 | Brown et al. | |
| 5,639,924 A | 6/1997 | Elsheikh et al. | |
| 5,679,875 A * | 10/1997 | Aoyama | B01J 23/24 570/156 |
| 6,022,823 A | 2/2000 | Augustine et al. | |
| 2002/0038065 A1 | 3/2002 | Huang et al. | |
| 2006/0217579 A1 | 9/2006 | Bailey | |
| 2007/0123741 A1* | 5/2007 | Van Der Puy et al. | 570/123 |

FOREIGN PATENT DOCUMENTS

| | | | |
|---|---|---|---|
| CN | 1086840 A | 5/1994 | |
| EP | 0644173 A1 | 3/1995 | |

OTHER PUBLICATIONS

Webpage: http://digitalfire.com/4sight/material/calcined_alumina_41.html, downloaded May 14, 2015.*

Shirai et al., Ceramics Research Laboratory, NITECH (2009) "Structural Properties and Surface Characteristics on Aluminum Oxide Powders", vol. 9, 23-31.*

I. L. Knunyants et al., Comparison of the Reactivity of the Simplest Olefins and Fluoroolefins in Catalytic Hydrogenation, Institute of Heteroorganic Compounds, Academy of Sciences of the USSR. Translated. pp. 708-713, Aug. 19, 1966. RU.

I. L. Knuyants et al., Mechanism of Interaction of Fluoro-Olefins With Hydrogen on the Surface of Metallic Catalysts, Institute of Heteroorganic Compounds, Academy of Sciences of the USSR. Translated. pp. 1091-1098, Aug. 19, 1966. RU.

I.L. Knunyants et al., Reactions of Fluoro Olefins. 13. Catalytic Hydrogenation of Perfluoro Olefins, Institute of Heteroorganic Compounds, Academy of Sciences of the USSR. Translated. pp. 1412-1418, Jan. 1, 1960. RU.

P. M. Kating et al., Hydrogenation of Fluoroolefins Studied by Gas Phase NMR: A New Technique for Heterogeneous Catalysis, J. Am. Chem. Soc. 1996, vol. 118, pp. 10000-10001. US.

Supplementary European Search Report issued in EP10806914 dated Apr. 2, 2013. EP.

Sykora, Milan, Chemicky Prumysl (1971), 21(11), 546-50, the DERWENT abstract is provided.

Thomas Allmendinger et al., The Hydrogenation of Fluoroolefins. Central Research Laboratories, Ciba-Geigy AG, CH 4002 Basel Switzerland. As reprinted in Tetrahedron Letters, vol. 32, No. 24, pp. 2735-2736, 1991 GB.

Corresponding—Office Action in Mexican Application No. MX/a/2012/001543, dated Nov. 25, 2013—enclosing record of prior art search result.

Chinese Search Report issued in CN201080044150.2 dated Oct. 10, 2013.

Alvin B. Stiles, "Catalyst Supports and Supported Catalysts: Theoretical and Applied Concepts," Butterworth Publisher, 1987 (Chapter 2, pp. 11-55).

* cited by examiner

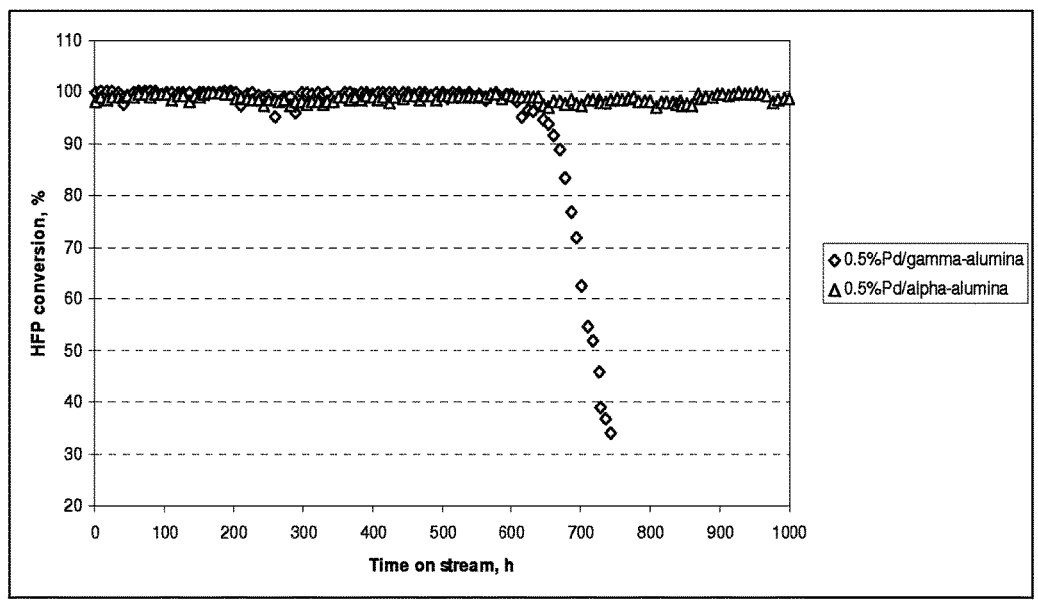

HYDROGENATION CATALYST

BACKGROUND

1. Field of Invention

The present invention relates to catalysts for hydrogenating olefins. More particularly, this invention relates to supported catalyst for hydrogenating fluoroolefins.

2. Description of Prior Art

Catalytic hydrogenation of fluoroolefins is frequently used in producing hydrofluorocarbons as useful products and/or intermediates. Various metals, such as Pd, supported on a substrate have long been recognized as highly effective hydrogenation catalysts. These catalysts are particularly effective in gas-phase reactions. Alumina is known as a support for these catalysts. Alumina has several different phases, typically designated by different Greek letters, e.g., alpha ($\alpha$) (also known as corundum), beta ($\beta$), chi ($\chi$), kappa ($\kappa$), eta ($\eta$), theta ($\theta$), delta ($\delta$), and gamma ($\lambda$). Each has a unique crystal structure and properties. For example, alpha alumina is composed of hexagonal crystals, whereas gamma alumina is composed of cubic crystals. (http://www.infoplease.com/ce6/sci/A0803541.html).

Aluminas other than alpha phase alumina are known as transitional phases because they can be transformed to the alpha form at high temperatures. Id. Other forms of alumina include amorphous alumina (that is, alumina lacking a crystalline structure) and activated alumina which is a highly porous form of dehydrated alumina that has a large specific surface area—often significantly over 200 square meters/g. (http://en.wikipedia.org/wiki/Activated_alumina).

Typically, preferred supports are characterized by a high specific surface area. For example, U.S. Pat. No. 2,657,980 states that "[i]n contrast with activated alumina is the well-known form of alumina known as corundum [alpha-alumina], which is not microporous and is unsuitable for [use as a hydrogenation catalyst]." See also, U.S. Pat. No. 2,908,654 (Stating that, "It has not been feasible to employ corundum (sometimes called alpha alumina) as a carrier for highly reactive reforming catalyst, and in order to distinguish from corundum, catalyst carrier grades are designated by terms such as activated alumina, sorptive alumina or gamma alumina.") Amorphous alumina has also been reported as a support for hydrogenation catalysts. (U.S. Pat. No. 2,875,158).

Low concentration palladium/silver catalysts supported on alpha-alumina have been reported as hydrogenation catalyst for selectively hydrogenating acetylene. (U.S. Pat. No. 4,404,124) In contrast, other phases of alumina have been reported as hydrogenation catalyst for alkenes, particularly fluoroalkenes. For example, I. L. Knunyants and E. I. Mysov (Kinetika i Kataliz, Vol. 8, No. 4, pp. 834-840) reported a Pd/Al$_2$O$_3$ catalyst with a specific surface of about 200 m$^2$/g for the hydrogenation of CF$_2$=CF$_2$ to CHF$_2$CHF$_2$, and CF$_3$CF=CF$_2$ (HFP) to CF$_3$CHFCHF$_2$ (236ea). Based on the surface area information, the alumina used in this catalyst can be one of transition aluminas.

However, due to the occurrence of hydrogenolytic cleavage of the carbon-fluorine bond, a small amount of HF is generated during hydrogenation of fluoroolefin which can attack the transition alumina catalyst support causing catalyst structure change and catalyst deactivation. Thus, all known transition alumina supports for metal catalysts are inclined to be attacked by HF in the hydrogenation of fluoroolefins, thereby limiting the useful lifetime. Accordingly, there remains a need for a long-lived catalyst support for a catalyst useful in hydrogenating fluoroolefins. This invention satisfies this need among others.

SUMMARY OF THE INVENTION

Applicants unexpectedly found that metal catalysts supported on alpha-alumina, which is the ultimate product of these transition aluminas under high temperature calcination and is characterized by small specific surface area (normally below 50 m$^2$/g), provided stable activity for the hydrogenation of fluoroolefins, while those supported on transition alumina such as gamma-alumina exhibited unstable activity.

Accordingly, in one aspect of the invention provided is a composition comprising (a) about 90 to about 99.9 of alumina, wherein said alumina is at least about 90 wt. % alpha-alumina; and (b) about 0.1 to about 10 weight percent of at least one metal, wherein said metal is selected from the group consisting of Pd, Ru, Pt, Rh, Ir, Fe, Co, Ni, Cu, Ag, Re, Os, Au, and any combinations thereof.

According to another aspect of the invention, provided is an article of manufacture comprising a supported hydrogenation catalyst, wherein said supported hydrogenation catalyst comprises (a) a support comprising alpha-alumina and having at least one surface, and (b) at least one zero-valent metal disposed on at least a portion of said surface, wherein said zero-valent metal is present in an amount from about 0.1 to about 10 weight percent based upon the total weight of the support and reduced zero-valent metal.

According to another aspect of the invention, provided is a method for preparing a catalyst comprising (a) contacting at least one metal salt, at least one solvent, and alpha-alumina to form a slurry; (b) removing said solvent from said slurry to form a solvent-free powder; (c) optionally calcining said powder; (d) transforming said powder into a supported catalyst; and (e) contacting said support catalyst with a gaseous composition comprising H$_2$ to activate said supported catalyst, wherein said activated supported catalyst comprises about 90 to about 99.9 weight percent dehydrated alpha-alumina and about 0.1 to about 10 weight percent of a zero-valent metal derived from said metal salt. In certain preferred embodiments, the method comprises the steps of (a) dissolving a salt of metal component (e.g., Pd(NO$_3$)$_2$, PdCl$_2$ for Pd) in a suitable solvent to form a solution; (b) adding a suitable amount of alpha-alumina into said solution to form a slurry; (c) driving off the solvent from said slurry to form a paste; (d) drying said paste to form solvent-free powder; (e) calcining said solvent-free powder in N$_2$ flow for 2 to 8 hours at 300-500° C.; (f) grinding the calcined powder to a finely divided state; (g) palletizing said fine powder into tablets; and (h) reducing said catalyst pellets in H$_2$ or diluted H$_2$ flow for 2 to 4 hours at 150-250° C. prior to use.

According to yet another aspect of the invention, provided is a method for hydrogenating a compound comprising contacting a reactant comprising an olefin, wherein said olefin has at least one carbon-fluorine bond, with a supported hydrogenation catalyst under reaction conditions effective to form a reaction product comprising a hydrogenated derivative of said olefin; wherein said supported hydrogenation catalyst comprises a zero-valent metal disposed on a support comprising alpha-alumina. Preferably, the method involves hydrogenating a fluoroolefin or hydrofluoroolefin, and more preferably involves hydrogenating a fluoroolefin or hydrofluoroolefin to produce a hydrofluoroalkane. In a preferred embodiment, the method comprises the steps of (a) adding hydrogen and a fluoroolefin to a reaction vessel containing a hydrogenation catalyst; and (b) reacting said fluoroolefin with hydrogen over said hydrogenation catalyst to produce a hydrofluorocarbon. Non-limiting examples of hydrofluorocarbons that can be produced through the hydrogenation of certain fluoroolefins include 1,1,1,2,3,3-hexafluoropropane (236ea), 1,1,1,2,3-pentafluoropropane (245eb), 1,1,1,3,3-pentafluoropropane (245fa), 1,1,1,3-tetrafluoropropane (254fb), and 1,1,1,2-tetrafluoropropane (254eb).

BRIEF DESCRIPTION OF THE DRAWING

FIG. 1 shows 1,1,1,2,3,3-hexafluoropropene (HFP) conversion versus time on stream during HFP hydrogenation over 0.5 wt % Pd/gamma-alumina and 0.5 wt % Pd/alpha-alumina catalysts.

DETAILED DESCRIPTION OF PREFERRED EMBODIMENTS OF THE INVENTION

According to a preferred embodiment of the invention, alpha-alumina supported metal catalysts are employed in the hydrogenation of fluoroolefins to hydrofluorocarbons. Non-limiting examples of metal components include Pd, Ru, Pt, Rh, Ir, Fe, Co, Ni, Cu, Ag, Re, Os, Au, and any combinations thereof. The metal loading can vary within a large range, e.g., from 0.1-10 wt %. However, for noble metals such as Ru, Ph, Pd, Pt, Ir, etc., the metal loading is preferably about 0.1 to about 5 wt %, and more preferably about 0.1 to about 1 wt %. It has been discovered that supported catalyst having metal concentrations below about 0.1 wt. % are not highly effective at hydrogenating fluoroolefins or hydrofluoroolefins.

In one embodiment, the salt of a metal component (e.g., $Pd(NO_3)_2$ or $PdCl_2$ for Pd) is added to an amount of solvent sufficient to substantially dissolve or solubilize the metal salt. The preferred solvent is one in which the metal salt is readily soluble. The choice of solvent may vary depending on the particular metal salts. Examples of solvents that can be used for the preparation of the catalyst compositions of the present invention include water, alcohols, ethers, and mixtures thereof. Useful alcohols include monohydric and polyhydric alcohols. Most preferred alcohols are those that are monohydric and have 1 to 5 carbon atoms. A most preferred solvent is water.

Desired amount of alpha-alumina powder is added to the solution of said metal salt to form a slurry. After formation of the slurry, substantially all of the solvent is removed to form a solid mass of a mixture of said metal salt and said alpha-alumina. Although the solvent can be removed in one step, a preferred method is to drive off a portion of the solvent from the slurry to form a paste and then followed by drying the paste to form the solid mass. Any conventional technique can be used to drive off the solvent. Examples of such techniques include vigorous stirring at room or elevated temperatures, evaporation, settling and decanting, centrifugation, and filtration. It is preferred to evaporate off a desired amount of solvent to form the paste. The paste is then dried by any suitable method to form a free-flowing, substantially solvent-free powder. Preferred methods for drying include oven drying, most preferably at temperatures from about 110° C. to about 120° C., and spray drying. As used herein, the term "solvent free" means that less than 1 wt. %, preferably about 0.5 wt % or less, more preferably about 0.1 wt % or less, and most preferably no solvent will remain with the powder after solvent removal/drying. Upon removal of solvent, the powder will take the form of a solid mass (or powder) of a mixture of particles of said metal salt and said alpha-alumina.

Optionally, the solid mass of the mixture of said metal salt and said alpha-alumina powder is then calcined. Calcination is preferably carried out at a temperature of about 100° C. to about 750° C., more preferably at a temperature of about 200° C. to about 600° C., and most preferably at a temperature of about 300° C. to about 500° C. Calcination may further optionally be carried out in the presence of an inert gas, such as nitrogen or argon.

After calcination, the powder is optionally further grinded such that it becomes more finely-divided. The powder is further optionally pelletized in order to form pellets.

The catalyst pellets are then loaded into a reactor and prior to use are reduced in hydrogen or diluted hydrogen flow for 2-4 hours at a temperature of about 50 to about 500° C., more preferably at a temperature of about 100 to about 300° C., and most preferably at a temperature of about 150 to about 250° C.

Although it is contemplated that the hydrogenation of fluoroolefins may be conducted in batch operation, it is preferred that the hydrogenation reaction is carried out as a substantially continuous operation. Furthermore, while it is possible that the hydrogenation reaction may involve in certain embodiments a liquid phase reaction, it is contemplated that in preferred embodiments the hydrogenation reaction comprises, and even more preferably consists of, at least two vapor phase reaction stages.

With respect to the number of reaction stages, applicants have found surprisingly and unexpectedly that overall reaction conversion and selectivity can be achieved at relatively high levels by the use of at least two reaction stages wherein the first stage of reaction is conducted under conditions effective to achieve a first, relatively low rate of conversion to produce a first stage reaction effluent, and at least a second stage of reaction which is fed by at least a portion of said first stage effluent and which is conducted under conditions effective to achieve a second rate of conversion higher than said first rate. Preferably, reaction conditions are controlled in each of the first and second stages in order to achieve the desired conversion in accordance with the present invention. As used herein, the term "reaction conditions" is intended to include the singular and means control of any one or more processing parameters which can be modified by the operator of the reaction to produce the conversion of the feed material in accordance with the teachings contained herein. By way of example, but not by way of limitation, conversion of the feed material may be controlled or regulated by controlling or regulating any one or more of the following: the temperature of the reaction, the flow rate of the reactants, the presence of diluent, the amount of catalyst present in the reaction vessel, the shape and size of the reaction vessel, the pressure of the reaction, and any combinations of these and other process parameters which will be available and known to those skilled in the art in view of the disclosure contained herein.

Applicants have found that in preferred embodiments the step of controlling the conversion in the first stage of the hydrogenation reaction is achieved by judicious selection and control of the amount of catalyst present in the first stage of reaction relative to the feed rate of one or more of the reactants and/or by judicious selection and control of the reaction temperature, and preferably by judicious selection and control of both of these process parameters. The step of judiciously selecting the amount of catalyst to be used in the first stage of reaction includes the step of estimating the amount of catalyst theoretically needed to convert 100% of the feed material. Such an estimate can be obtained by any and all known methods for making such an estimate, which should be apparent to those skilled in the art in view of the teachings contained herein. In addition, the step of judiciously selecting the amount of catalyst may also involve conducting bench, pilot or similar studies to determine the amount of the particular catalyst being used which is needed to convert 100% of the feed material under the feed rate in other process parameters which have otherwise been chosen. Based upon this estimate, the preferred embodiments of the present invention then include the step of providing in the first stage of reaction an amount of catalyst that is substantially below the amount required for 100% conversion, and even more preferably is sufficiently low so as to result in a conversion of the feed olefin of from about 10% to about 60%, more preferably from about 10% to about 40%, and even more preferably from about 10% to 25%. Once again, those skilled in the art will appreciate that the step of judiciously choosing the amount of catalyst may further include running additional bench, pilot or other studies with the reduced amount of catalyst and adjusting the amount of catalyst accordingly. It is contemplated that all such studies and estimates can be achieved without undue experimentation in view of the teachings contained herein.

Applicants have found that the step of maintaining a relatively low conversion of reactant in accordance with the present invention in a first stage of reaction has an advantageous affect on the selectivity of the reaction to the desired hydrofluorocarbon. In other words, although the amount of conversion which occurs in the first stage of reaction is controlled to be well below that which is desired for the overall hydrogenation step, applicants have found that an improved, higher percentage of the feed material is converted to the desired hydrofluorocarbon in the first reaction stage (that is, improved selectivity is achieved) by controlling the conversion as described herein. More specifically, it is preferred in many embodiments that the selectivity to the desired hydrofluorocarbon in the first reaction stage is at least about 80%, more preferably at least about 90%, and even more preferably at least about 95%, and in many preferred embodiments about 97% or greater.

In certain preferred embodiments the step of controlling the conversion in the first reaction stage further includes removing heat from the reaction by cooling at least a portion of the reaction mixture. It is contemplated that those skilled in the art will be able to devise without undue experimentation and many means and mechanisms for attaining such cooling in view of the teachings contained herein and all such means and mechanisms are with the scope of the present invention.

In preferred embodiments, at least a portion of the effluent from the first reaction stage is fed directly, or optionally after some further processing, to a second reaction stage in which the unreacted fluoroolefin remaining in the effluent after the first reaction stage is converted to the hydrofluorocarbon in accordance with the present invention. More specifically is preferred that the second reaction stage or subsequent reaction stages if present, is operated under conditions effective to convert the fluoroolefin contained in the feed stream to the second reactor stage at a conversion rate that is greater than, and preferably substantially greater than, the conversion percentage in the first reaction stage. In certain preferred embodiments, for example, the conversion percentage in the second reaction stage is from about 20% to about 99%, depending in large part upon the total number of reactant stages used to affect the overall conversion step. For example, in embodiments consisting of a two-stage reaction system, it is contemplated that the conversion in the second reaction stage is preferably greater than 95%, and even more preferably about 100%. However, as those skilled in the art will appreciate from the teachings contained herein, such a two-stage reaction may not be sufficient to produce the desired selectivity to the hydrofluorocarbon. In such cases, it is within the scope of the present invention that the conversion step may comprise greater than two reaction stages, including in some embodiments as many 10 or more reaction stages.

The size and shape, and other characteristics of the reaction vessel itself may vary widely with the scope of the present invention, and it is contemplated that the vessel associated with each stage may be different than or the same as the vessel associated with the upstream and downstream reaction stages. Furthermore, it is contemplated that all reaction stages can occur inside a single vessel, provided that means and mechanisms necessary to control conversion are provided. For example, it may be desirable in certain embodiments to utilize a single tubular reactor for each reaction stage, providing conversion control by judicious selection of the amount and/or distribution of catalyst throughout the tubular reactor. In such a case, it is possible to further control the conversion in different sections of the same tubular reactor by controlling the amount of heat removed from or added to different sections of the tubular reactor.

The catalyst compositions disclosed in the present invention are useful in converting fluoroolefins to hydrofluorocarbons. The catalysts are stable because of their resistance to HF attack and can be re-used after regeneration. One or more of the hydrogenation catalyst disclosed in the present invention may be used for one or more of the reaction stages in accordance with the present invention.

Thus, certain embodiments of the present methods comprise bringing a fluoroolefin and a hydrogenation agent, such as $H_2$, into contact with a first amount of catalyst in a first reaction stage to produce a reaction stream comprising hydrofluorocarbon(s), unreacted fluoroolefin and hydrogen; contacting at least a portion of this first effluent stream with a second amount of catalyst in a second stage of reaction to produce a hydrofluorocarbon, wherein the second amount of catalyst is greater than the first amount of catalyst and wherein conversion to the fluoroolefin is higher in the second stage of reaction.

Table 1 sets forth examples of hydrofluorocarbons and fluoroolefins from which they can be obtained (fluoroolefin in left column and corresponding hydrofluorocarbon in the right column).

TABLE 1

| Fluoroolefins | Hydrofluorocarbons |
| --- | --- |
| 1,1,2,3,3,3-hexafluoropropene $CF_3CF=CF_2$ (1216) | 1,1,1,2,3,3-hexafluoropropane $CF_3CHFCHF_2$ (236ea) |
| 1,2,3,3,3-pentafluoropropene $CF_3CF=CHF$ (Z/E-1225ye) | 1,1,1,2,3-pentafluoropropane $CF_3CHFCH_2F$ (245eb) |
| 1,1,3,3,3-pentafluoropropene $CF_3CH=CF_2$ (1225zc) | 1,1,1,3,3-pentafluoropropane $CF_3CH_2CHF_2$ (245fa) |
| 1,3,3,3-tetrafluoropropene $CF_3CH=CHF$ (trans/cis-1234ze) | 1,1,1,3-tetrafluoropropane $CF_3CH_2CH_2F$ (254fb) |
| 2,3,3,3-tetrafluoropropene $CF_3CF=CH_2$ (1234yf) | 1,1,1,2-tetrafluoropropane $CF_3CHFCH_3$ (254eb) |

EXAMPLES

The following are examples of the invention and are not to be construed as limiting.

Example 1

Comparison of Gamma-Alumina and Alpha-Alumina Supported Pd Catalysts for 1,1,1,2,3,3-Hexafluoropropene Hydrogenation 0.5 wt % Pd/gamma-alumina and 0.5 wt % Pd/alpha-alumina, which have a specific surface area of 243 and 33 $m^2/g$, respectively, were compared for 1,1,1,2,3,3-hexafluoropropene (HFP) hydrogenation. About 2 g of catalyst diluted with 20 ml of Monel packing was charged into a ¾" Monel tube reactor and was in-situ reduced in 10% $H_2/N_2$ flow for 2 hours at 200° C. HFP was fed into reactor at a rate of 5 g/h, and $H_2$ was co-fed according to a mole ratio of $H_2$/HFP equal to 1.5. As shown in Table 2, both catalysts initially provided a near complete HFP conversion and a 236ea selectivity of above 99.5%. Nevertheless, as shown in FIG. 1, while no deactivation was noted over the 0.5 wt % Pd/alpha-alumina catalyst even after 1000 h on stream, rapid deactivation was observed over the 0.5 wt % Pd/gamma-alumina beginning around 600 h on stream. This indicates that the alpha-alumina supported Pd catalyst is much more stable than the gamma-alumina supported Pd catalyst.

TABLE 2

HFP hydrogenation over alumina supported Pd catalysts*

| Catalyst | Temp. (° C.) | Conversion, % HFP | Selectivity, % 236ea | Selectivity, % others |
| --- | --- | --- | --- | --- |
| 0.5% Pd/γ-alumina | 100 | 99.9 | 99.6 | 0.4 |
| 0.5% Pd/α-alumina | 100 | 98.2 | 99.9 | 0.1 |

*data obtained after 2 h on stream.

Example 2

Hydrogenation of 1,1,1,2,3,3-Hexafluoropropene Over Alpha-Alumina Supported Pd Catalyst 0.5 wt % Pd/alpha-alumina catalyst, which has a specific surface area of 33 $m^2/g$, was used for 1,1,1,2,3,3-hexafluoropropene (HFP) hydrogenation. About 1 g of catalyst diluted with 10 ml of Monel packing was charged into a ¾" Monel tube reactor and was in-situ reduced in 10% $H_2/N_2$ flow for 2 hours at 200° C. HFP was fed into reactor at a rate of 65 g/h, and $H_2$ was co-fed according to a mole ratio of $H_2$/HFP equal to 1.5. GC analysis of the product stream showed that the catalyst provided an HFP conversion of around 55% and a 245eb selectivity of about 99.5%. No deactivation was noted during the period of time of the test which lasted for 800 hours, indicating the alpha-alumina supported Pd catalyst can provide stable activity for HFP hydrogenation.

Example 3

Hydrogenation of 1,1,1,2,3-Pentafluoropropene Over Alpha-Alumina Supported Pd Catalyst 0.5 wt % Pd/alpha-alumina catalyst, which has a specific surface area of 33 $m^2/g$, was used for 1,1,1,2,3-pentafluoropropene (1225ye) hydrogenation. About 0.5 g of catalyst diluted with 10 ml of Monel packing was charged into a ¾" Monel tube reactor and was in-situ reduced in 10% $H_2/N_2$ flow for 2 hours at 200° C. 1225ye was fed into reactor at a rate of 30 g/h, and $H_2$ was co-fed according to a mole ratio of $H_2$/1225ye equal to 1.5. GC analysis of the product stream showed that the catalyst provided a 1225ye conversion of around 45% and a 245eb selectivity of about 98.5%. No deactivation was noted during the period of time of the test which lasted for 800 hours, indicating the alpha-alumina supported Pd catalyst can provide stable activity for 1225ye hydrogenation.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claim.

What is claimed is:

1. A method for hydrogenating a compound comprising: contacting a reactant comprising pentafluoropropene and/or hexafluoropropene, with a supported hydrogenation catalyst under reaction conditions effective to form a reaction product comprising a hydrogenated derivative of said pentafluoropropene and/or hexafluoropropene, wherein said supported hydrogenation catalyst comprises from 0.5 to about 10 weight percent of zerovalent palladium disposed on a support comprising about 90 percent by weight to about 99.5 percent by weight of alpha-alumina.

2. The method of claim 1 wherein said support consists essentially of alpha-alumina.

3. The method of claim 1 wherein said contacting comprises feeding said pentafluoropropene and/or hexafluoropropene into a first stage of a hydrogenation reactor at a rate resulting in a conversion of the feed pentafluoropropene and/or hexafluoropropene of from about 10% to about 60%.

4. The method of claim 3 wherein said reaction product further comprises at least a portion of said pentafluoropropene and/or hexafluoropropene from said reactant that remains unreacted subsequent to said contacting; and wherein said method further comprises converting, in one or more subsequent stages of said hydrogenation reactor, about 20 to about 100 percent of said pentafluoropropene and/or hexafluoropropene in said reaction product into said hydrogenated derivative of said pentafluoropropene and/or hexafluoropropene.

5. The method of claim 4 wherein said support consists essentially of alpha-alumina.

6. The method of claim 1 wherein said hydrogenation catalyst comprises about 0.5 weight percent of said zerovalent Pd.

7. The method of claim 1 wherein said olefin is selected from the group consisting of 1,1,2,3,3,3-hexafluoropropene; 1,2,3,3,3-pentafluoropropene; and 1,1,3,3,3-pentafluoropropene.

8. The method of claim 1 wherein said hydrogenated derivative of said olefin is selected from the group consisting of 1,1,1,2,3,3-hexafluoropropane; 1,1,1,2,3-pentafluoropropane; and 1,1,1,3,3-pentafluoropropane.

9. The method of claim 1 wherein said olefin comprises 1,1,2,3,3,3-hexafluoropropene and said hydrogenated derivative of said olefin comprises 1,1,1,2,3,3-hexafluoropropane.

10. The method of claim 1 wherein said olefin comprises 1,2,3,3,3-pentafluoropropene and said hydrogenated derivative of said olefin comprises 1,1,1,2,3-pentafluoropropane.

* * * * *